(12) United States Patent
Iftime et al.

(10) Patent No.: US 11,585,771 B2
(45) Date of Patent: Feb. 21, 2023

(54) METAL NANOPARTICLE-DECORATED NANOTUBES FOR GAS SENSING

(71) Applicant: Palo Alto Research Center Incorporated, Palo Alto, CA (US)

(72) Inventors: Gabriel Iftime, Dublin, CA (US); Clinton Smith, San Francisco, CA (US); David Eric Schwartz, San Carlos, CA (US); Yong Zhang, Millbrae, CA (US); Vedasri Vedharathinam, Sunnyvale, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 17/677,716

(22) Filed: Feb. 22, 2022

(65) Prior Publication Data

US 2022/0178859 A1    Jun. 9, 2022

Related U.S. Application Data

(62) Division of application No. 16/996,239, filed on Aug. 18, 2020, now Pat. No. 11,327,036, which is a (Continued)

(51) Int. Cl.
*G01N 27/04* (2006.01)
*B01J 20/20* (2006.01)
(Continued)

(52) U.S. Cl.
CPC .......... *G01N 27/04* (2013.01); *B01J 20/0225* (2013.01); *B01J 20/205* (2013.01); *B01J 20/3204* (2013.01); *B01J 20/327* (2013.01);
*G01N 27/126* (2013.01); *G01N 27/127* (2013.01); *G01N 33/0009* (2013.01); *B22F 1/102* (2022.01); *B22F 2999/00* (2013.01);
(Continued)

(58) Field of Classification Search
CPC ...... G01N 27/04; B01J 20/0225; B01J 20/205
See application file for complete search history.

(56) References Cited

U.S. PATENT DOCUMENTS 5,618,493 A     4/1997  Goldstein et al.
2006/0188723 A1  8/2006  Rowley et al.
(Continued)

OTHER PUBLICATIONS

Extended European Search Report dated Aug. 20, 2018 for European Patent Application No. 18166837.7.
(Continued)

*Primary Examiner* — Alvaro E Fortich
(74) *Attorney, Agent, or Firm* — Womble Bond Dickinson (US) LLP

(57) ABSTRACT

Disclosed herein are methods of producing metal nanoparticle-decorated carbon nanotubes. The methods include forming a reaction mixture by combining a first solution with a second solution, wherein the first solution comprises polymer-coated metal nanoparticles comprising metallic nanoparticles coated with a polymer, and wherein the second solution comprises carbon nanotubes. The methods also include heating the reaction mixture to a temperature greater than a glass transition temperature of the polymer for a time sufficient to cause the polymer-coated metal nanoparticles to bind to the carbon nanotubes forming the metal nanoparticle-decorated carbon nanotubes.

19 Claims, 8 Drawing Sheets

Related U.S. Application Data division of application No. 15/582,172, filed on Apr. 28, 2017, now Pat. No. 10,830,721.

(51) Int. Cl.

| | |
|---|---|
| *B01J 20/02* | (2006.01) |
| *B01J 20/32* | (2006.01) |
| *G01N 33/00* | (2006.01) |
| *G01N 27/12* | (2006.01) |
| B82Y 30/00 | (2011.01) |
| B82Y 40/00 | (2011.01) |
| B82Y 15/00 | (2011.01) |
| C22C 26/00 | (2006.01) |
| B22F 1/102 | (2022.01) |

(52) U.S. Cl.
CPC .............. *B82Y 15/00* (2013.01); *B82Y 30/00* (2013.01); *B82Y 40/00* (2013.01); *C22C 2026/002* (2013.01)

(56) References Cited

U.S. PATENT DOCUMENTS

| | | | |
|---|---|---|---|
| 2007/0259437 A1 | 11/2007 | Natan et al. | |
| 2008/0150556 A1 | 6/2008 | Han et al. | |
| 2010/0255290 A1* | 10/2010 | Bai ................... | B82Y 30/00 204/157.41 |
| 2012/0156099 A1 | 6/2012 | Zhong et al. | |
| 2012/0161787 A1* | 6/2012 | Potyrailo ............... | G01N 27/02 29/595 |
| 2012/0280174 A1 | 11/2012 | Atieh et al. | |
| 2012/0298925 A1* | 11/2012 | Kim ..................... | C08L 101/12 977/773 |
| 2013/0065319 A1 | 3/2013 | Zang et al. | |
| 2013/0115137 A1 | 5/2013 | Tao et al. | |
| 2013/0243874 A1 | 9/2013 | Sun et al. | |
| 2014/0070170 A1* | 3/2014 | Andersson ......... | G01N 27/4146 257/29 |
| 2014/0095102 A1 | 4/2014 | Potyrailo et al. | |
| 2015/0021716 A1 | 1/2015 | Lee et al. | |
| 2015/0065363 A1 | 3/2015 | Johnson, Jr. et al. | |
| 2016/0054659 A1 | 2/2016 | Shin et al. | |
| 2016/0195488 A1 | 7/2016 | Ensor et al. | |
| 2016/0195504 A1* | 7/2016 | Swager ............... | B81C 1/00031 438/49 |
| 2016/0202225 A1 | 7/2016 | Feng et al. | |
| 2017/0092388 A1 | 3/2017 | Lee et al. | |
| 2017/0221645 A1 | 8/2017 | Gangopadhyay et al. | |
| 2017/0254767 A1 | 9/2017 | Karasawa et al. | |

OTHER PUBLICATIONS

Cardoso et al., "A Facile Strategy to Support Palladium Nanoparticles on Carbon Nanotubes, Employing Polyvinylpyrrolidone as a Surface Modifier", European Journal of Inorganic Chemistry, 2014, pp. 1439-1445.

Choi et al., "Noxious gas detection using carbon nanotubes with Pd nanoparticles", Nanoscale Research Letters, vol. 6, 2011, pp. 605-610.

Jeong, "Surface functionalization of single-walled carbon nanotubes using metal nanoparticles", Transactions of Nonferrous Metals Society of China, vol. 19, 2009, pp. 1009-1012.

Patole et al., "Carbon nanotubes with silver nanoparticle decoration and conductive polymer coating for improving the electrical conductivity of polycarbonate composites", Carbon, vol. 81, 2015, pp. 720-730.

Rajesh et al., "Recent progress in the development of nano-structured conducting polymers/nanocomposites for sensor applications", Sensors and Actuators B, vol. 136, 2009, pp. 275-286.

Zhang et al., "Carbon Nanotubes as Active Components for Gas Sensors", Journal of Sensors, vol. 2009, Article ID 160698, 16 pages.

Ju, Seonghwa, et al., "Highly sensitive hydrogen gas sensors using single-walled carbon nanotubes grafted with Pd nanoparticles" Sensors and Actuators B: Chemical, 2010, 7 pages.

Santra, Subhankar, et al., "Anchored palladium nanoparticles onto single walled carbon nanotubes: Efficient recyclable catalyst for N-containing heterocycles", RSC Advances, 2012, 11 pages.

Atieh, Muataz Ali, et al., "Effect of Carboxylic Functional Group Functionalized on Carbon Nanotubes Surface on the Removal of Lead from Water", Bioinorganic Chemistry and Applications, 2010, Hindawi Publishing Corporation, 9 pages.

Cornelio, Benedetta, et al., "Palladium nanoparticles on carbon nanotubes as catalysts of cross-coupling reactions", Journal of Materials Chemistry A, 2013, RSC Publishing, 8 pages.

Hei, Huixiao, et al., "Controlled Synthesis and Characterization of Noble Metal Nanoparticles", Scientific Research, Department of Chemistry and Chemical Engineering, Beijing University of Technology, Jul. 2012, Beijing, China, 7 pages.

Wang, Zhaowei, "The surface acidity of acid oxidised multi-walled carbon nanotubes and the influence of in-situ generated fulvic acids on their stability in aqueous dispersions", Carbon 47, School of Pharmacy and Biomolecular Sciences, University of Brighton, 2009, United Kingdom, 7 pages.

Carrillo, Alvaro, et al., Noncovalent Functionalization of Graphite and Carbon Nanotubes with Polymer Multilayers and Gold Nanoparticles, 2003.

* cited by examiner

METAL NANOPARTICLE-DECORATED NANOTUBES FOR GAS SENSING

RELATED APPLICATIONS

The present application is a divisional of U.S. patent application Ser. No. 16/996,239, filed Aug. 18, 2020, entitled "METAL NANOPARTICLE-DECORATED NANOTUBES FOR GAS SENSING", which is a divisional of U.S. patent application Ser. No. 15/582,172, filed Apr. 28, 2017, entitled "METAL NANOPARTICLE-DECORATED NANOTUBES FOR GAS SENSING," which issued on Nov. 10, 2020 as U.S. Pat. No. 10,830,721, the entire contents of which are incorporated by reference herein.

STATEMENT REGARDING FEDERALLY SPONSORED RESEARCH AND DEVELOPMENT

This invention was made with government support under Contract No. DE-AR0000542 MONITOR-SPHINCS awarded by the Advanced Research Projects Agency-Energy. The Government has certain rights in this invention.

TECHNICAL FIELD

The presently disclosed embodiments are directed to gas sensors, and, more particularly, nanoparticle-based materials for gas sensors.

BACKGROUND

Various techniques are utilized for gas leak detection, with each approach having advantages trade-offs. Such techniques include, for example, catalytic bead sensors, metal-oxide-semiconductor (MOS) sensors, non-dispersive infrared sensors, and infrared laser-based sensors.

Catalytic bead and MOS sensors are compact and can easily be integrated into printed circuit boards. They also have high methane detection limits, which are sufficient for improving safety, but insufficient for detecting low level leaks that, when undetected, can add up and have an adverse environmental effect. Moreover, these sensors consume enough power to not be compatible with long-term battery powered operation, and suffer from interference from similar gases since they utilize chemical interactions to perform their measurements.

Infrared-based sensors are highly sensitive and generally immune to interference, but are often expensive, bulky, and have high power requirement.

SUMMARY

The following presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its sole purpose is to present some concepts of the disclosure in a simplified form as a prelude to the more detailed description that is presented later.

In one aspect of the present disclosure, a composition comprises: carbon nanotubes having an average degree of functionalization with carboxylic acid groups and/or hydroxyl groups that is less than 3 percent by weight (wt %) based on a total weight of the carbon nanotubes; and polymer-coated metal nanoparticles bound to the carbon nanotubes.

In one embodiment, the polymer-coated metal nanoparticles are non-covalently bound to the carbon nanotubes.

In one embodiment, the carbon nanotubes are substantially free of carboxylic acid functional groups and hydroxyl functional groups.

In one embodiment, the carbon nanotubes comprise single-walled carbon nanotubes or multi-wall carbon nanotubes.

In one embodiment, the polymer-coated metal nanoparticles each comprise a metallic core and a polymer layer covalently bound to the metallic core. In one embodiment, the polymer layer comprises a hydrophobic polymer. In one embodiment, the metallic core comprises a metal selected from a group consisting of palladium, iridium, rhodium, platinum, and gold. In one embodiment, the polymer layer comprises poly(vinylpyrrolidinone), and wherein the metallic core comprises palladium.

In one embodiment, the composition is dispersed in an organic solvent.

In another aspect of the present disclosure, a sensor for detecting gas comprises: an electrode assembly comprising electrodes; and a gas-adsorbing material disposed between the electrodes of the electrode assembly. In one embodiment, the gas-adsorbing material comprises: carbon nanotubes; and polymer-coated metal nanoparticles bound to the carbon nanotubes.

In one embodiment, the electrode assembly is operatively coupled to a processing device, wherein the processing device is to measure changes in resistivity of the gas-adsorbing material that result from gas molecules adsorbed to the gas-adsorbing material. In one embodiment, the sensor has detection limit of 100 parts per million (ppm) during operation in an ambient environment having a relative humidity from 0% to 80%. In one embodiment, the sensor is adapted to selectively detect methane.

In one embodiment, the polymer-coated metal nanoparticles are non-covalently bound to the carbon nanotubes.

In one embodiment, an average degree of functionalization of the carbon nanotubes with carboxylic acid groups and/or hydroxyl groups is less than 3 wt % based on a total weight of the carbon nanotubes.

In another aspect of the present disclosure, a method of producing metal nanoparticle-decorated carbon nanotubes comprises: forming a reaction mixture by combining a first solution with a second solution, wherein the first solution comprises polymer-coated metal nanoparticles comprising metallic nanoparticles coated with a polymer, and wherein the second solution comprises carbon nanotubes; and heating the reaction mixture to a temperature greater than a glass transition temperature of the polymer for a time sufficient to cause the polymer-coated metal nanoparticles to bind to the carbon nanotubes forming the metal nanoparticle-decorated carbon nanotubes.

In one embodiment, the polymer-coated metal nanoparticles are fully-formed prior to forming the reaction mixture.

In one embodiment, the polymer-coated metal nanoparticles are non-covalently bound to the carbon nanotubes.

In one embodiment, an average degree of functionalization of the carbon nanotubes with carboxylic acid groups and/or hydroxyl groups is less than 3 wt % based on a total weight of the carbon nanotubes.

In one embodiment, the method further comprises dispersing the metal nanoparticle-decorated carbon nanotubes in a non-aqueous solvent-based ink.

BRIEF DESCRIPTION OF THE DRAWINGS

The present disclosure is illustrated by way of example, and not by way of limitation, in the figures of the accompanying drawings, in which.

DETAILED DESCRIPTION

Figure 1:
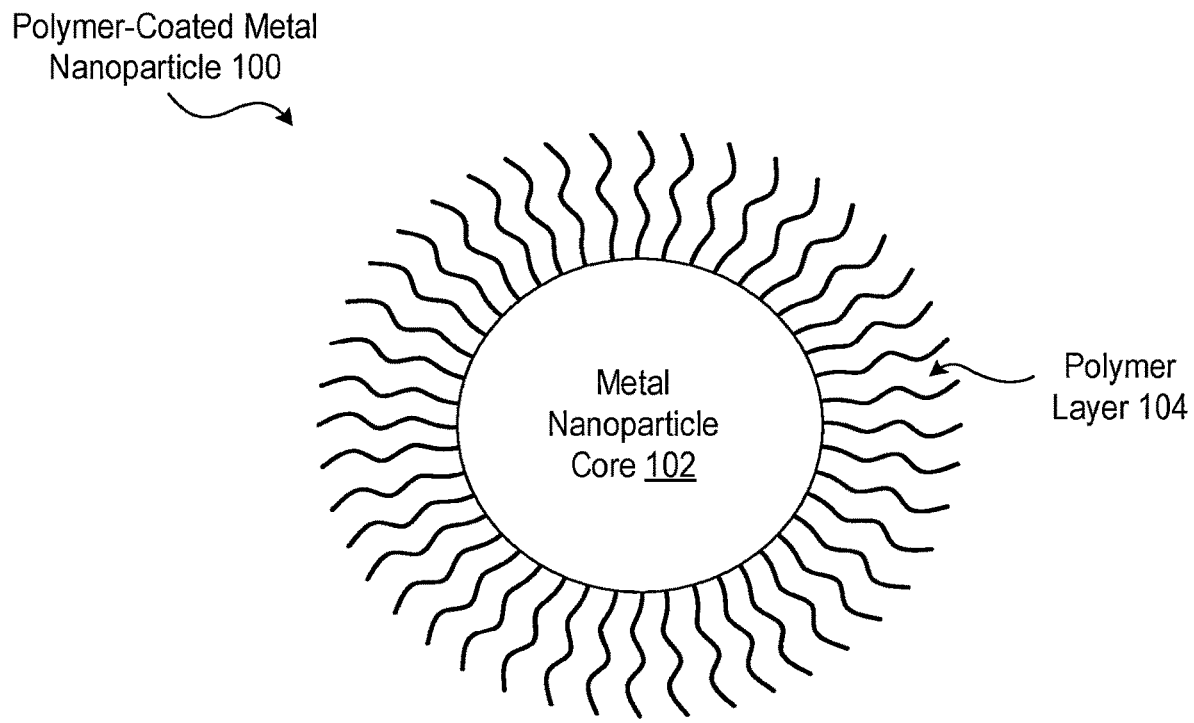
FIG. 1 is an illustration of an embodiment of a polymer-coated metal nanoparticle.

Described herein are embodiments of metal nanoparticle-decorated nanotubes, methods for producing the same, and sensors incorporating the same. Certain embodiments relate to a gas (e.g., methane) sensor that uses a hydrophobic composition comprising carbon nanotubes (e.g., single-walled carbon nanotubes, or "SWCNTs") decorated with metal nanoparticles as a sensing material. The sensing material (also referred to herein as a "gas-adsorbing material") may be placed in between interdigitated electrodes of a sensor. When methane gas adsorbs to the sensing material, its electronic state is changed resulting in a change in resistivity that is proportional to the amount of methane adsorbed. This change in resistivity can be measured via a number of resistivity measurement techniques (e.g., voltammetry). The sensor, when adapted for methane sensing, can be regenerated by flushing with methane-free gas.

Current approaches to detect methane focus on creating extremely compact and low power devices. These approaches focus on the adsorptive effects of different types of materials. This includes catalytic metal-decorated carbon nanotubes, thin films utilizing catalytic metals, and graphene or carbon nanotube with chemical modifications. However, such physisorption-based methane sensors lose their detection capability in the presence of water vapor to the point that many cannot detect even pure methane mixed with water vapor. Since humidity is present everywhere in the atmosphere, current methane sensors based on adsorption effects cannot work reliably in practical situations.

Without being bound by theory, it is proposed herein that a reason for this performance loss is due to the accumulation of water onto adsorptive surfaces by interaction with the surface carboxylic acid groups or hydroxyl groups through hydrogen bonding. It is hypothesized that the interaction between methane and the metal nanoparticles is hydrophobic, and would be independent of the water vapor concentration if the presence of hydrophilic functional groups is reduced or suppressed entirely. As described herein, an approach to limit the impact of water vapor includes suppressing the available carboxylic acid ("—COOH") sites for water vapor to adsorb to. This includes, for example, capping the —COOH groups with hydrophobic metal nanoparticles, as well using polymers to bind the nanoparticles to the nanotube (e.g., through non-covalent interactions).

In one embodiment, organic polymer-coated palladium nanoparticles (produced separately from the SWCNTs) are mixed with the SWCNTs and heated to a temperature above the glass transition temperature of the polymer. On cooling, it was found that palladium-decorated SWCNTs were obtained in the cases of highly —COOH-functionalized SWCNTs, SWCNTs with low —COOH functionalization, and even SWCNTs without any —COOH functionalization. This result is unexpected in view of previous approaches, which suggest the need for highly functionalized —COOH in order to grow Pd nanoparticles onto SWCNTs. Without being bound by theory, it is hypothesized that an additional mechanism by which the Pd particles bind onto the surfaces of the SWCNTs is due to heat-driven softening of the coating polymer present onto the Pd nanoparticles, allowing the Pd nanoparticles to be bound non-specifically and non-covalently to the SWCNTs.

The embodiments of the present disclosure provide low-power, low-cost alternatives to traditional methane sensing techniques that are capable of detecting leaks in virtually any environment, even those with high or variable humidity. Moreover, the embodiments of the present disclosure afford several advantages over traditional gas-sensing approaches. The embodiments utilizing printable metal nanoparticle-decorated nanotubes are capable of reliably detecting low concentrations of methane leaks in the presence of variable humidity levels. The embodiments are adaptable for use in portable or hand-held devices, or as part of a network of sensors in natural gas extraction fields. The embodiments can also be used for sensing other gases, for example, by replacing palladium with other metals such as, but not limited to, iridium, rhodium, platinum, or gold. In addition, the disclosed methods are modularized and easily scalable for mass production.

FIG. 1 is an illustration of an embodiment of a polymer-coated metal nanoparticle 100. The polymer-coated metal nanoparticle 100 includes a metallic core 102 and a polymer layer 104 that coats the metallic core 102. In some embodiments, the metallic core 102 may be crystalline, polycrystalline, amorphous, or a combination thereof. In some embodiments, the metallic core 102 may comprise a single metal species (e.g., a transition metal), or an alloy of different metal species. In some embodiments, the metal is selected from palladium, iridium, rhodium, platinum, and gold. For example, in specific embodiments for sensing methane, the metallic core 102 may be a palladium core. In certain embodiments, a diameter of the metallic core 102 may range, for example, from 1 nm to 100 nm, from 1 nm to 50 nm, from 1 nm to 20 nm, from 1 nm to 10 nm, or from 1 nm to 5 nm.

The polymer layer 104, as illustrated, comprises a plurality of linear polymers bound to a surface of the metallic core 102. In some embodiments, branched polymers may be used. In some embodiments, the polymers may be covalently bound to the metallic core 102. In other embodiments, the polymers may be physically adsorbed to the metallic core 102, with the adsorption being driven by, for example, hydrophobic interactions. The polymers may be densely packed on the surface of the metallic core 102 such that steric forces between the polymers cause the polymers to extend from the surface. The rigidity of the polymer layer may be a function of polymer chemical structure, packing density, surface curvature, polymer molecular weight and polydispersity, and solvent conditions. The polymer layer 104 may serve to mitigate inter-particle forces between the polymer-coated metal nanoparticle 100 and other polymer-coated metal nanoparticles to prevent aggregation while dispersed in solvent. In some embodiments, the polymer layer 104 comprises polymers of a single type or of different types. In some embodiments, the polymer layer 104 comprises hydrophobic polymers. In some embodiments, the polymer layer 104 comprises polyvinylpyrrolidone (PVP).

Figure 2:
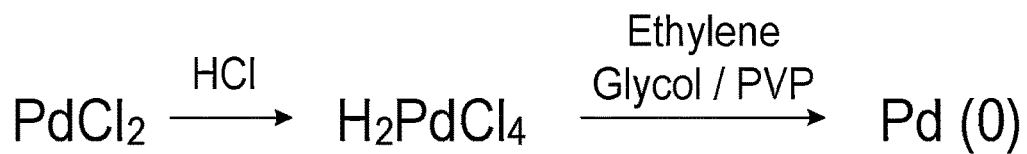
FIG. 2 illustrates a reaction process for producing polymer-coated metal nanoparticles according to one embodiment of the present disclosure.

FIG. 2 illustrates a reaction process for producing polymer-coated metal nanoparticles according to one embodiment of the present disclosure. Specifically, FIG. 2 illustrates a reaction process for producing PVP-coated palladium nanoparticles, where insoluble $PdCl_2$ is first reacted with HCl to form soluble $H_2PdCl_4$, which is then subsequently reacted with ethylene glycol in the presence of PVP to produce Pd(0) metal nanoparticles.

In certain embodiments, metal nanoparticle-decorated nanotubes are produced by a process utilizing a separate step for synthesizing the metal nanoparticles and a separate step for synthesizing nanotubes, which affords greater control over the end product than methods that grow the nanoparticles directly at functionalized locations on the nanotube surface.

As used herein, "nanotube" refers to a hollow structure having nanoscale dimensions along at least two axes. Nanotubes may be cylindrical in shape and have high aspect ratios, with diameters from, for example, 5 nanometers (nm) to 100 nm, and lengths that generally range from 20 nm to 1 micrometer (μm) or greater. Although single wall carbon nanotubes are described herein in exemplary embodiments, the embodiment s extend to other types of carbon nanotubes such as multi wall carbon nanotubes. The electronic properties of carbon nanotubes can vary from metallic to semiconducting as a function of diameter and chirality (which describes a degree of "twisting" in the positions of atoms along a length of the nanotube).

Figure 3:
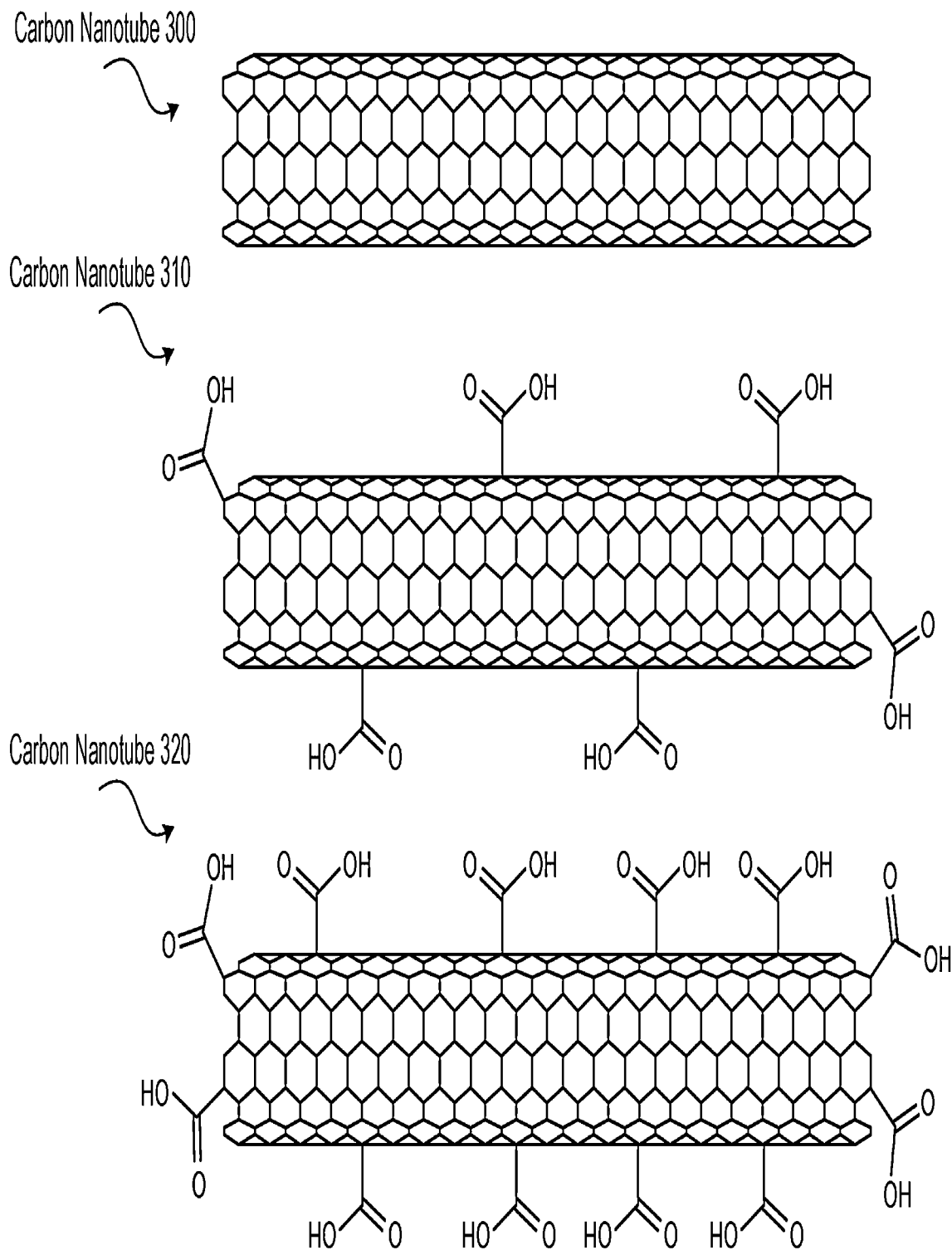
FIG. 3 is an illustration of carbon nanotubes with increasing amounts of carboxylic acid functionalization.

FIG. 3 is an illustration of carbon nanotubes with increasing amounts of carboxylic acid functionalization. Carbon nanotube 300 represents a carbon nanotube with no functionalization or minimal functionalization with —COOH or other hydrophilic functional groups. Carbon nanotube 310 represents a carbon nanotube with a low or moderate degree of —COOH functionalization, and carbon nanotube 320 represents a carbon nanotube with a high degree of —COOH functionalization. The —COOH may be present along the surface of the carbon nanotubes, as well as at the ends of the carbon nanotubes.

Figure 4:
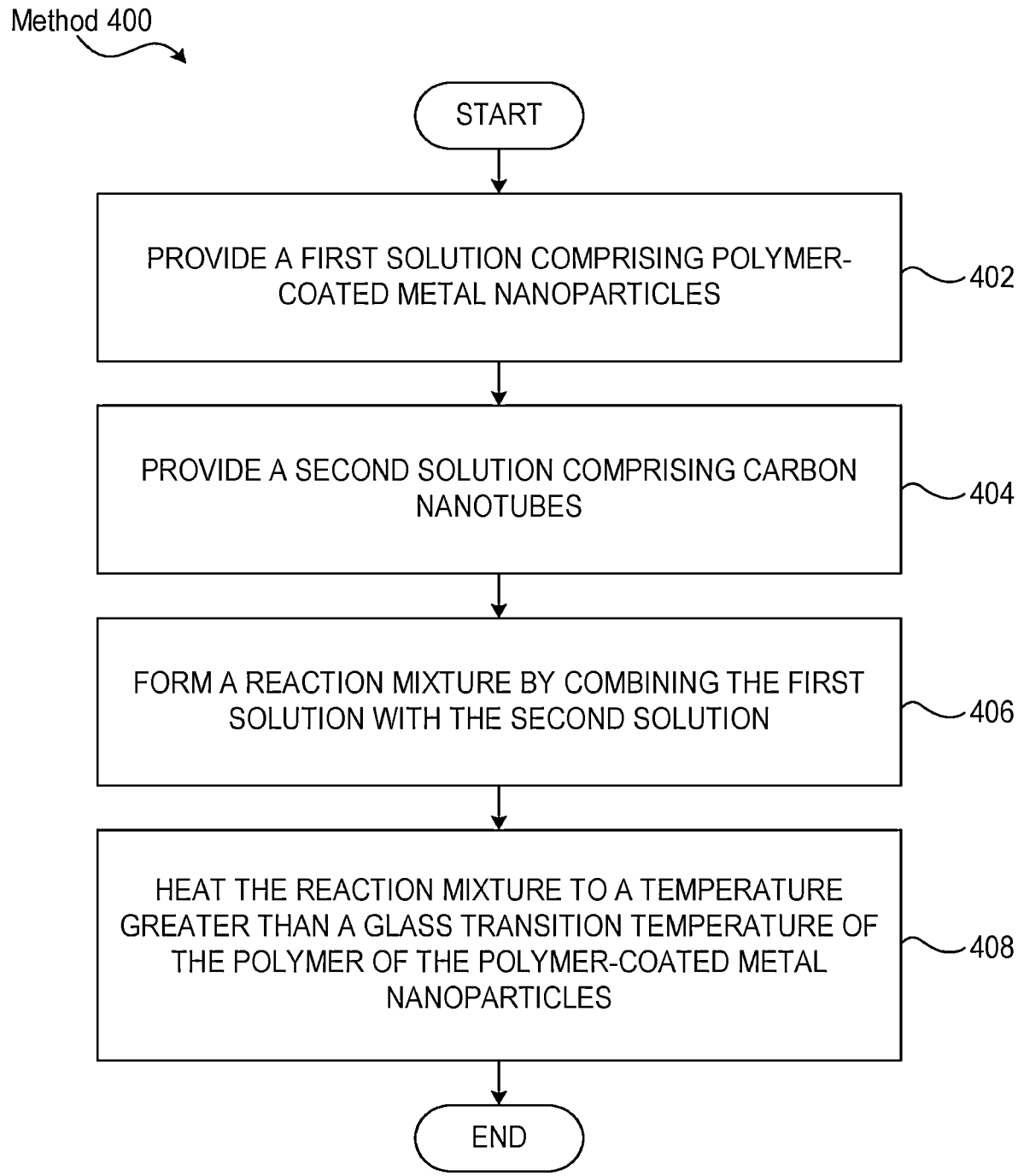
FIG. 4 is a flow diagram illustrating a method for producing a metal nanoparticle-decorated nanotube in accordance with embodiments of the present disclosure.

FIG. 4 is a flow diagram illustrating a method 400 for producing metal nanoparticle-decorated nanotubes in accordance with embodiments of the present disclosure. The method 400 begins at block 402, where a first solution comprising polymer-coated metal nanoparticles is provided. The polymer-coated metal nanoparticles may have structures represented by the polymer-coated metal nanoparticle 100 described with respect to FIG. 1. The polymer-coated metal nanoparticles may be synthesized as described herein (e.g., Example 4 below), or using any adaptations or other suitable synthesis methods as would be appreciated by one of ordinary skill in the art. In some embodiments, each polymer-coated metal nanoparticle comprises a palladium core and a polymer layer comprising PVP. In some embodiments, the polymer-coated metal nanoparticles are dispersed in an organic solvent.

At block 404, a second solution comprising carbon nanotubes is provided. The carbon nanotubes may be unfunctionalized, may be substantially free of carboxylic acid (—COOH) and/or hydroxyl (—OH) functionalization (e.g., below a detectable limit), or may have an average degree of —COOH and/or —OH functionalization less than 3% percent by weight (wt %) based on a total mass of the carbon nanotubes (i.e., including any such functionalization). In some embodiments, the carbon nanotubes may have an average degree of —COOH and/or —OH functionalization greater than or equal to 3 wt %. The wt % of —COOH and —OH functionalization, as discussed herein, is measured by the weight loss in thermogravimetric analysis (TGA) at temperatures below 300° C. when the measurement is run in Ultra High Purity (UHP) grade inert gas. The carbon nanotubes may be synthesized as described herein (e.g., Examples 1-3 below), or using any adaptations or other suitable synthesis methods as would be appreciated by one of ordinary skill in the art. In some embodiments, the carbon nanotubes are SWCNTs. In some embodiments, the carbon nanotubes are dispersed in an aqueous solvent.

Figure 5:
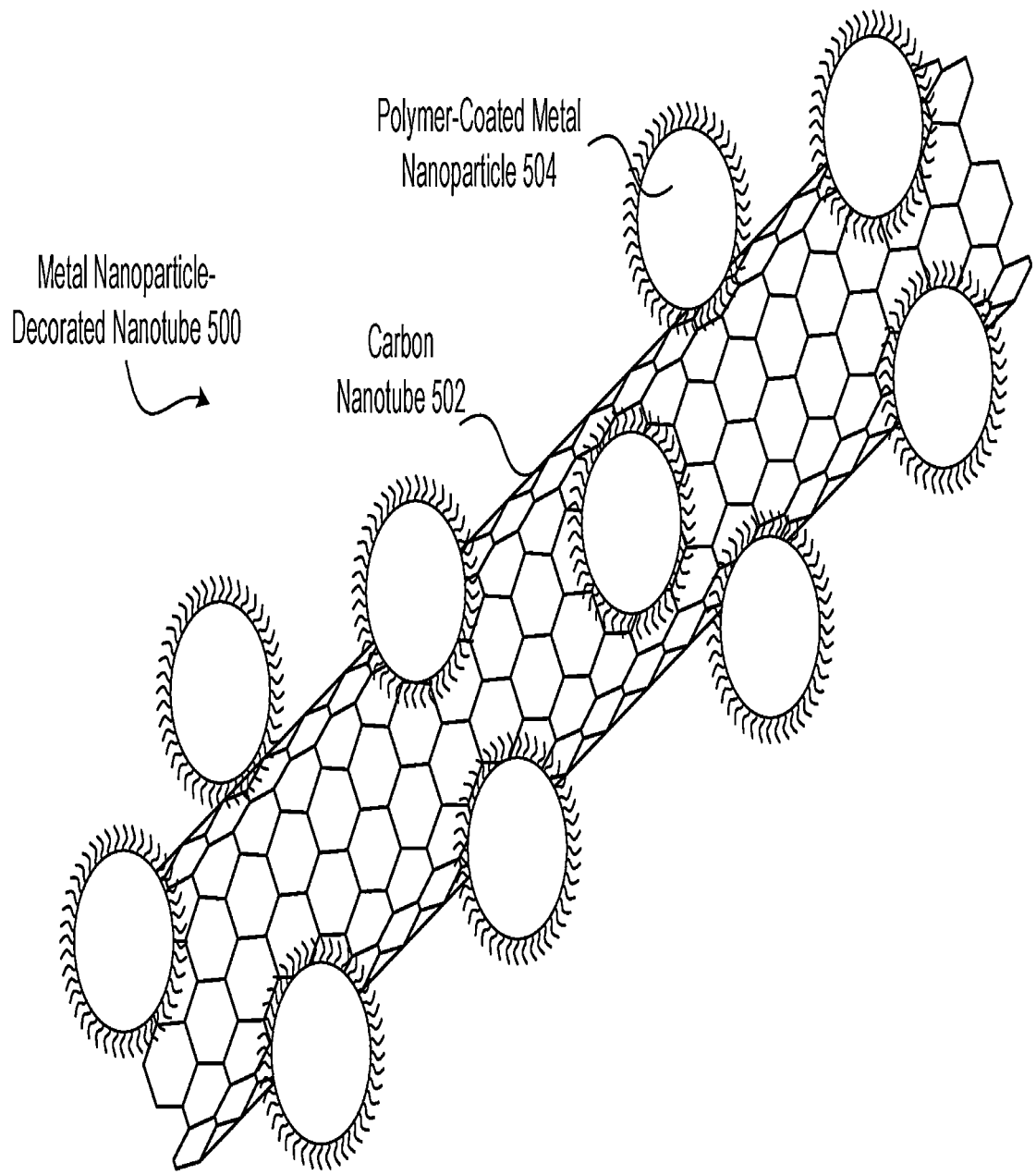
FIG. 5 is a schematic illustrating an exemplary metal nanoparticle-decorated nanotube produced in accordance with embodiments of the present disclosure.

At block 406, a reaction mixture is formed by combining the first solution with the second solution. At block 408, the reaction mixture is heated to a temperature greater than a glass transition temperature of the polymer of the polymer-coated metal nanoparticles (a glass transition temperature for PVP, for example, may vary from 100° C. to 180° C. depending on its molecular weight). In some embodiments, the temperature is greater than but within 50° C. of the glass transition temperature. In some embodiments the temperature is greater than but within 25° C. of the glass transition temperature. In some embodiments the temperature is greater than but within 10° C. of the glass transition temperature. In some embodiments, the temperature is from 120° C. to 180° C. In some embodiments, the temperature is from 120° C. to 140° C. In some embodiments, the temperature is from 150° C. to 180° C. In some embodiments, the temperature is maintained for a time duration of 30 minutes to 4 hours. In some embodiments, the temperature may be varied from one temperature (e.g., 120° C. to 140° C.) for a first time duration (e.g., 30 minutes to 4 hours) to a second temperature (150° C. to 180° C.) for a second time duration (e.g., 30 minutes to 4 hours). In some embodiments, the nanoparticle-coated metal nanoparticles are treated with a solvent to remove solvent-accessible PVP from surfaces of the nanoparticles. FIG. 5 illustrates an exemplary metal nanoparticle-decorated nanotube 500 having polymer-coated metal nanoparticles 504 bound to a carbon nanotube 502. The polymer-coated metal nanoparticles 504 are bound to the surface of the carbon nanotube 502 non-covalently by the adhesive nature of the polymer.

In certain embodiments, a sensor material for sensing methane gas may be produced (e.g., in accordance with the method 400) by immobilizing coated palladium nanoparticles on surfaces of SWCNTs with little to no —COOH functionalization, dispersing the resulting metal nanoparticle-decorated nanotubes in a non-aqueous solvent-based ink, and printing the ink onto a sensor chip.

Figure 6:
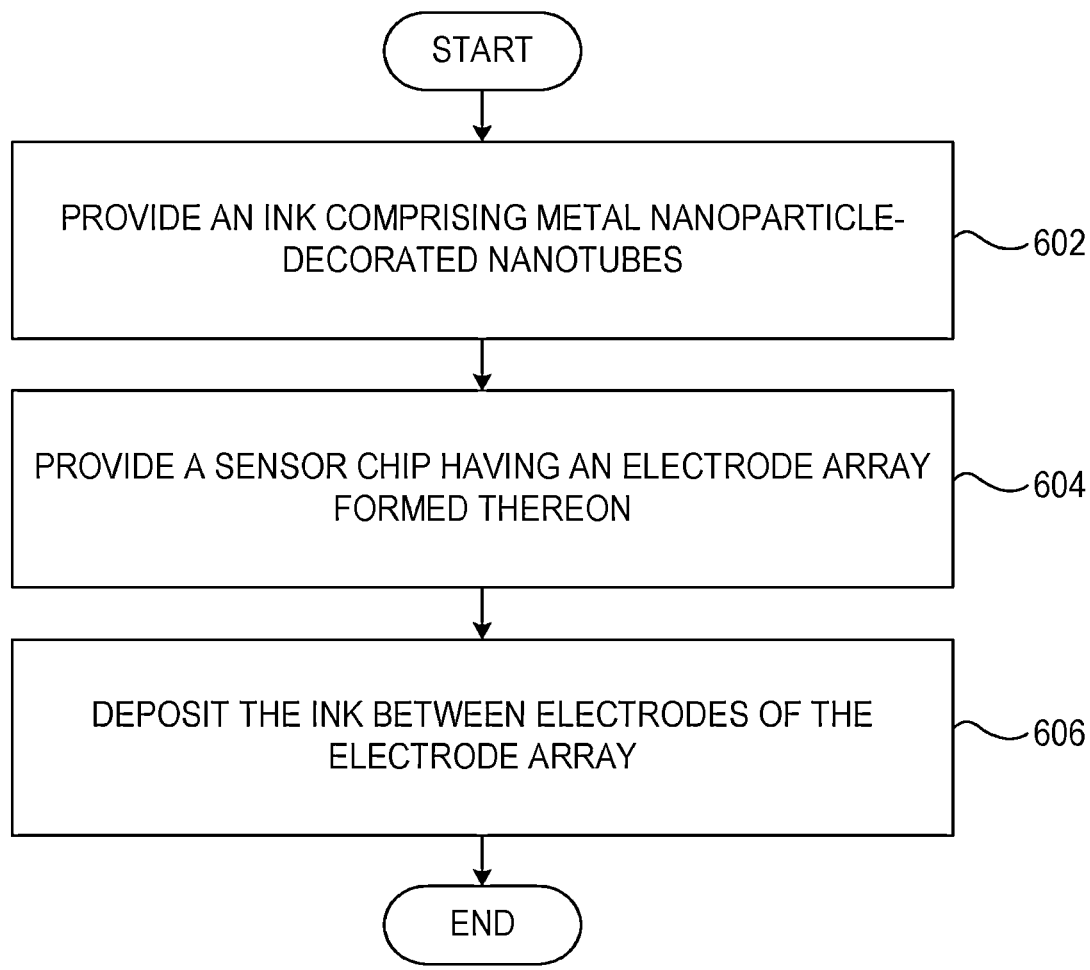
FIG. 6 is a flow diagram illustrating a method for fabricating a sensor in accordance with embodiments of the present disclosure.

FIG. 6 is a flow diagram illustrating a method 600 for fabricating a sensor in accordance with embodiments of the present disclosure. The method 600 begins at block 602, where an ink comprising metal nanoparticle-decorated nanotubes is provided. The metal nanoparticle-decorated nanotubes may correspond to any metal nanoparticle-decorated nanotubes described herein (e.g., PVP-coated palladium nanoparticles bound to SWCNTs).

At block 604, a sensor chip or substrate having an electrode array formed thereon is provided.

Figure 7A:
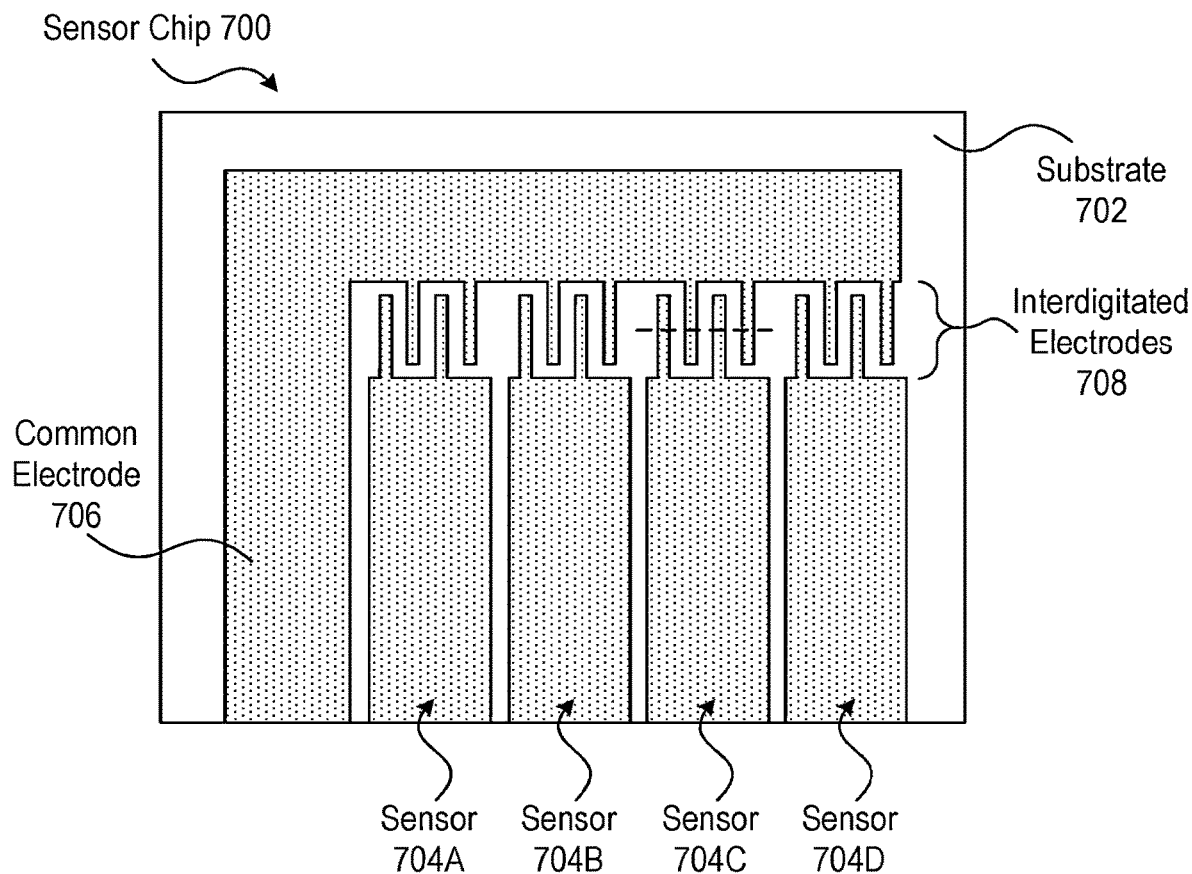
FIG. 7A is a schematic illustrating a top down view of an exemplary sensor chip according to an embodiment of the present disclosure.
Figure 7B:
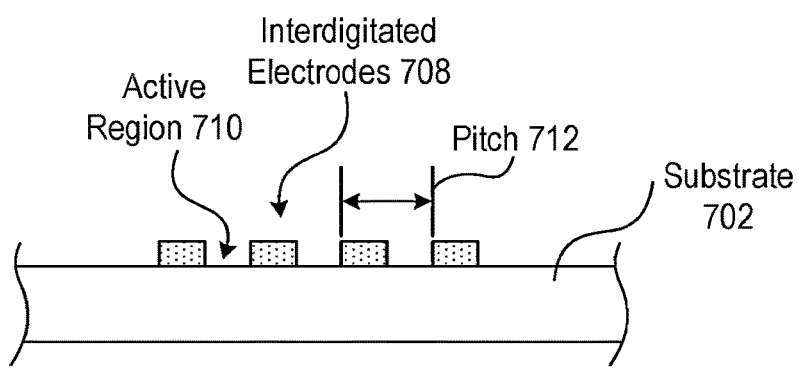
FIG. 7B is a schematic illustrating a cross-sectional view of the sensor chip.

Reference is now made to FIGS. 7A and 7B, which are schematics illustrating top down and cross-sectional views, respectively, of an exemplary sensor chip 700 according to an embodiment of the present disclosure. The sensor chip 700 includes a substrate 702 having sensors 704A-704D formed thereon. Although four sensors are depicted, it is noted that any suitable number of sensors may be used. The substrate 702 comprises a non-conductive material, such as polyethylene naphthalate (PEN), polyimide, or any other suitable non-conductive material. In some embodiments, a thickness of the substrate may be selected to facilitate a secure connection to a type of zero insertion force (ZIF) connector (e.g., substrate thickness of 250 µm).

The sensors 704A-704D may comprise any suitable electrode material such as copper, graphite, titanium, silver, gold, platinum, or combinations thereof. The sensors 704A-704D may be shaped to facilitate electrical contact with external components for sensor readout. A single counter electrode 706 may also be formed on the substrate 702, which may be shared by each of the sensors 704A-704D to reduce the total number of electrodes on the sensor chip 700.

The sensors 704A-704D and the common electrode 706 may together define a region with interdigitated electrodes 708. FIG. 7B illustrates a cross-section through the interdigitated electrodes 708 of the sensor 704C (as indicated by the dotted line in FIG. 7A), which shows an active region 710 defined between the interdigitated electrodes 708 where a gas-sensing material may be deposited. In certain embodiments, a thickness of the interdigitated electrodes 708 may range from 100 nm to 1 µm. A pitch 710 between adjacent interdigitated electrodes 708 may range, for example, from 50 µm to 5 mm.

The sensor chip 700 may be designed such that a portion of the sensor chip 700 can be directly inserted into an electrical connector for resistance measurement. In order to achieve desired resistance levels of the printed substance, the sensor chip 700 can be designed to vary the number, duty cycle, and dimensions (including thickness) of interdigitated electrodes 708, as well as the gap distance between adjacent electrodes. The dimensions of the printed leads of the sensors 704A-704D may be chosen such that the lead resistances for the common electrode path and the sensor path are nearly in order to cancel out their influence in the resistance measurements. The substrate 702 may be designed for ratiometric 3-wire resistance measurements, but may also be compatible with traditional 3-wire resistance measurements and 2-wire resistance measurements.

Figure 7C:
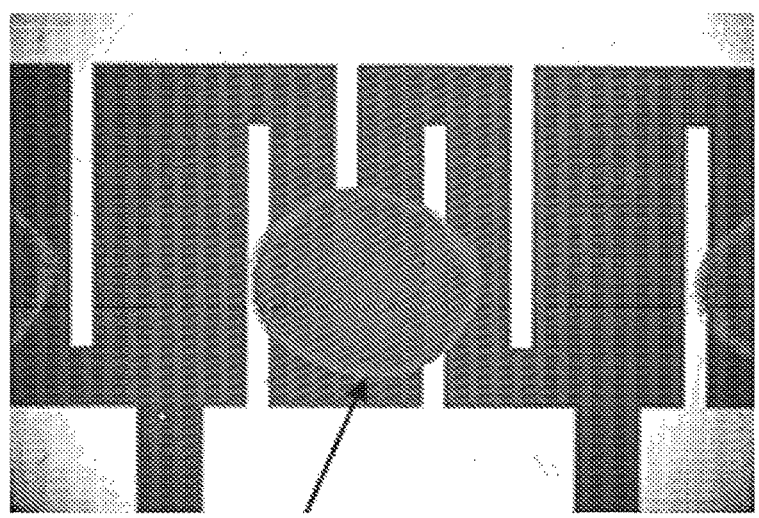
FIG. 7C is a micrograph showing an ink containing metal nanoparticle-decorated nanotubes that was printed onto interdigitated electrodes of an exemplary sensor.

Referring once again to FIG. 6, at block 606, the ink is deposited between electrodes of the electrode array, and the solvent of the ink is allowed to evaporate leaving a gas-sensing material comprising metal nanoparticle-decorated nanotubes. In certain embodiments, the ink is deposited by printing directly (e.g., using inkjet printing) on the sensors. In some embodiments, the ink is deposited using other suitable methods, such as pipetting, spin-coating, or dip-coating. FIG. 7C is a micrograph showing the ink printed onto interdigitated electrodes of an exemplary sensor.

Figure 7D:
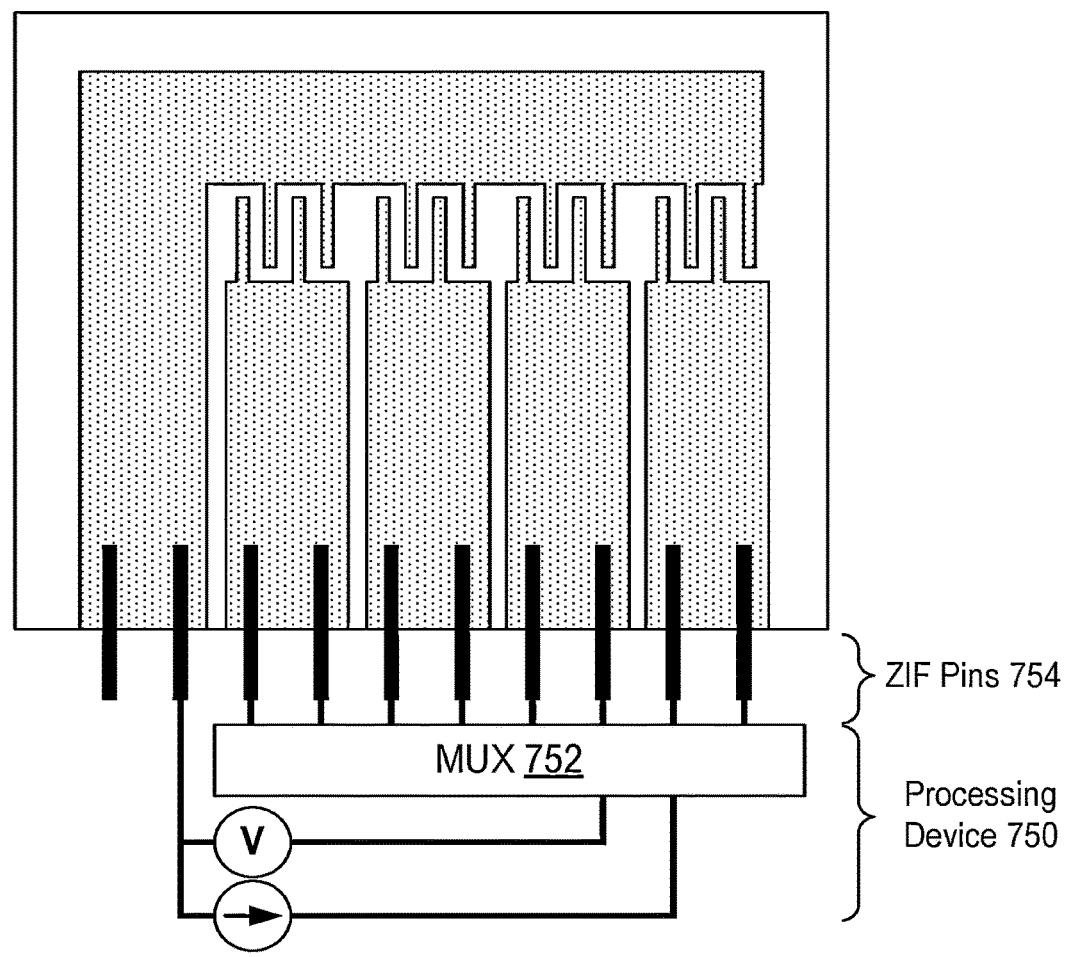
FIG. 7D is a schematic illustrating the sensor chip operatively coupled to a processing device according to an embodiment of the present disclosure.

FIG. 7D illustrates the operation of the sensor chip 700, which is illustrated as being operatively coupled to a processing device 750 (e.g., via a plurality of ZIF pins 754). The processing device may include one or more electronic components, such as a MUX 752, that may be configured to measure the resistivity of the gas sensing material using the various on-chip sensors. In some embodiments, the processing device 750 represents one or more general-purpose processing devices such as a microprocessor, central processing unit, or the like. For example, the processing device 750 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 750 may also be one or more special-purpose processing devices such as an application specific integrated circuit (ASIC), a field programmable gate array (FPGA), a digital signal processor (DSP), network processor, or the like. The processing device 750 may be configured to perform various operations, such as applying electrical signals, measuring electrical signals, and computing data based on the measured electrical signals. In certain embodiments, the processing device 750 may be a single device or a device that controls other devices. For example, the processing device 750 may be configured to perform resistivity measurements, or may control one or more other devices that perform resistivity measurements.

In some embodiments, a sensor produced according to the method 600 may operate over a wide relative humidity range in ambient conditions. As used herein, "ambient conditions" refers to the conditions of a typical laboratory environment with a temperature of 20±5° C. and a pressure of 1±0.1 atmospheres (ATM). In certain embodiments, during operation of the sensor in an ambient environment having a relative humidity from 0% to 80%, the sensor has a methane detection limit of 100 ppm. In some embodiments, the sensor may have a lower detection limit, e.g., 50 ppm or 10 ppm. The sensor may achieve such performance over a temperature range outside of the ambient conditions (e.g., from −5° to 50° C.).

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1: Fabrication of SWCNTs with High Degree of —COOH Functionalization

A suspension was produced by dispersing 200 mg of SWCNTs (NanoAmor) in 50 mL of deionized water and sonicating for 2 hours (20 W). The suspension was then placed in a round bottom flask and 50 mL of concentrated $HNO_3$ (16 M) were added. The reaction volume was refluxed under magnetic stirring at 120° C. for 5 days, and then cooled down to room temperature. The reaction volume was washed with deionized (DI) water and centrifuged to separate the particles. The washing and centrifugation process was repeated until neutral pH was reached.

Example 2: Fabrication of SWCNTs with Low Degree of —COOH Functionalization

The process from Example 1 was repeated except that after the reaction volume was heated and stirred for 2 hours instead of 5 days.

Example 3: Fabrication of SWCNTs with Negligible —COOH Functional Groups

A suspension was produced by dispersing 200 mg of SWCNTs (NanoAmor) in 100 mL of concentrated hydrochloric acid and bath sonicated for 30 minutes at room temperature. The suspension was diluted with 2 L water (deionized water filtered under vacuum using a 0.2 μm polytetrafluoroethylene membrane) and washed with deionized water until neutral pH was reached. The filtered material was then dispersed in 40 mL deionized water for later use.

Example 4: Fabrication of Polymer-Coated Metal Nanoparticles

Polymer-coated palladium (Pd) nanoparticles were synthesized using the polyol reduction method: a reaction volume was prepared in a Schleck flask by mixing 1.5 mL of 65 mM $H_2PdCl_4$ with 5 mL of 5 wt % polyvinylpyrrolidone (PVP) in ethylene glycol (EG) solution and adding 100 mL of EG. The reaction volume was saturated with argon followed by degassing in vacuum 5 times to remove dissolved oxygen. The PVP-coated Pd nanoparticles were then produced by heating the degassed solution at 130° C. for 3 h followed by 160° C. for 1 hour while stirring at 500 rpm. FIG. 7A is an electron micrograph showing the resulting PVP-coated Pd nanoparticles.

Example 5: Fabrication of Polymer-Coated Metal Nanoparticle-Decorated SWCNTs The Pd nanoparticle solution of Example 4 was cooled to room temperature after which 20 mL of SWCNTs dispersed in water was added to the Pd nanoparticle solution and degassed, followed by heating the degassed solution at 130° C. for 3 h and heating at 160° C. for 1 h while stirring. Excess acetone was added to the Pd-SWCNT solution and centrifuged at 4000 rpm for 10 min, and the supernatant solution was discarded to remove Pd-decorated SWCNTs (Pd-SWNTs). The particles were further washed with excess ethanol under stirring for 15 minutes followed by centrifugation at 4000 rpm for 10 minutes to remove the PVP from the Pd-SWCNT particles. The washing sequence was repeated five times.

Figure 8:
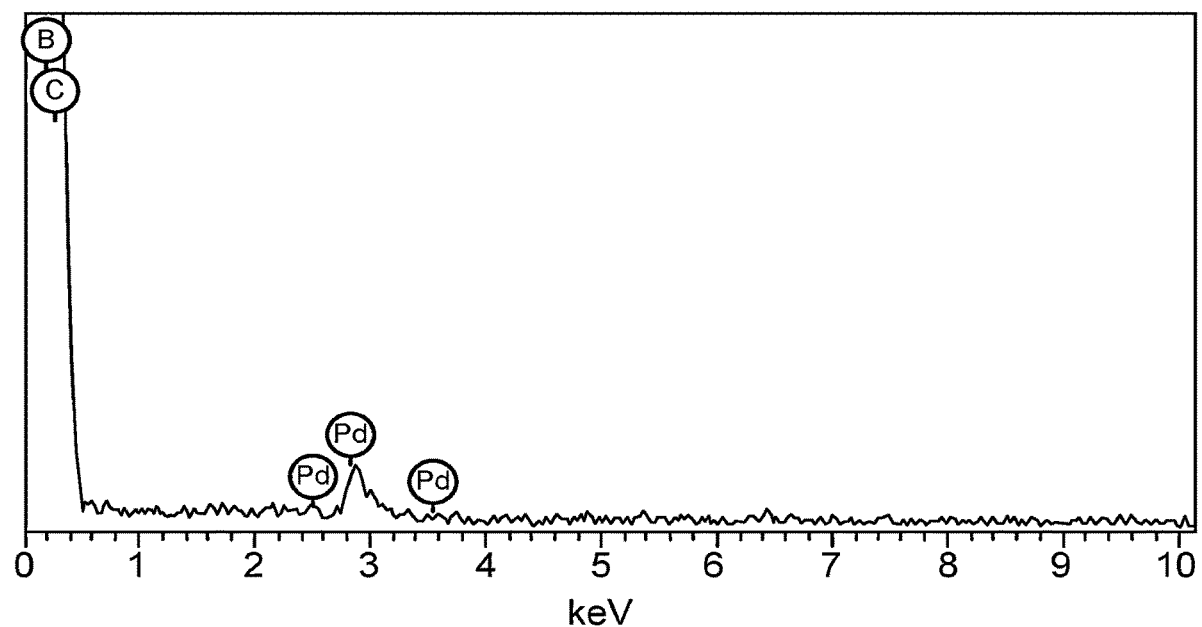
FIG. 8 is an energy-dispersive x-ray spectrum of metal nanoparticle-decorated nanotubes.

FIG. 8 is an energy-dispersive x-ray (EDX) spectrum of the Pd-SWCNT particles.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter.

Although embodiments of the disclosure were discussed in the context of composite materials (e.g., nanoparticle-nanotube composite materials) and devices utilizing the same for gas sensing, one or more of the components described herein may be adapted for use in other devices and systems. Thus, embodiments of the disclosure are not limited to gas sensors and the specific constituents described.

In the foregoing description, numerous details were set forth. It will be apparent, however, to one of ordinary skill in the art having the benefit of this disclosure, that the embodiments of the present disclosure may be practiced without these specific details. In some instances, certain structures and devices are shown in block diagram form, rather than in detail, in order to avoid obscuring the present disclosure. It is to be understood that the details of such structures and devices, as well as various processes for producing the same, would be within the purview of one of ordinary skill in the art.

The terms "above," "under," "between," and "on" as used herein refer to a relative position of one layer with respect to other layers. As such, for example, one layer deposited or disposed above or under another layer may be directly in contact with the other layer or may have one or more intervening layers. Moreover, one layer deposited or disposed between layers may be directly in contact with the layers or may have one or more intervening layers. In contrast, a first layer "on" or deposited "onto" a second layer is in contact with that second layer.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment" or "one embodiment" means that a particular feature, structure, or characteristic described in connection with the embodiment is included in at least one embodiment. Thus, the appearances of the phrase "an embodiment" or "one embodiment" in various places throughout this specification are not necessarily all referring to the same embodiment.

The present disclosure is not to be limited in scope by the specific embodiments described herein. Indeed, other various embodiments of and modifications to the present disclosure pertaining to nanocomposite materials and uses thereof, in addition to those described herein, will be apparent to those of ordinary skill in the art from the preceding description and accompanying drawings. Thus, such other embodiments and modifications thereto are intended to fall within the scope of the present disclosure. Further, although the present disclosure has been described herein in the context of a particular embodiment in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of producing metal nanoparticle-decorated carbon nanotubes, the method comprising:
   forming a reaction mixture by combining a first solution with a second solution, wherein the first solution comprises polymer-coated metal nanoparticles comprising metallic nanoparticles coated with a polymer, and wherein the second solution comprises carbon nanotubes; and
   heating the reaction mixture to a temperature greater than a glass transition temperature of the polymer for a time sufficient to cause the polymer-coated metal nanoparticles to bind to the carbon nanotubes forming the metal nanoparticle-decorated carbon nanotubes.

2. The method of claim 1, wherein the polymer-coated metal nanoparticles are fully-formed prior to forming the reaction mixture.

3. The method of claim 2, wherein the polymer-coated metal nanoparticles are non-covalently bound to the carbon nanotubes.

4. The method of claim 1, wherein an average degree of functionalization of the carbon nanotubes with carboxylic acid groups and/or hydroxyl groups is less than 3 wt % based on a total weight of the carbon nanotubes.

5. The method of claim 1, further comprising:
   dispersing the metal nanoparticle-decorated carbon nanotubes in a non-aqueous solvent-based ink.

6. The method of claim 1, wherein the polymer-coated-metal nanoparticles are coated with a hydrophobic polymer layer.

7. The method of claim 1, wherein the carbon nanotubes are substantially free of carboxylic acid functional groups and hydroxyl functional groups.

8. A method of producing metal nanoparticle-decorated carbon nanotubes, the method comprising:
   forming polymer-coated metal nanoparticles by dispersing a polymer and a salt precursor of a metal into a solvent, reducing the metal salt precursor of the metal with a reducing reagent;
   forming a reaction mixture by combining a first solution with a second solution, wherein the first solution comprises polymer-coated metal nanoparticles comprising metallic nanoparticles coated with a polymer, and wherein the second solution comprises carbon nanotubes; and
   heating the reaction mixture to a temperature greater than a glass transition temperature of the polymer for a time sufficient to cause the polymer-coated metal nanoparticles to bind to the carbon nanotubes forming the metal nanoparticle-decorated carbon nanotubes.

9. The method of claim 8, wherein an average degree of functionalization of the carbon nanotubes with carboxylic acid groups and/or hydroxyl groups is less than 3 wt % based on a total weight of the carbon nanotubes.

10. The method of claim 8, wherein the solvent is both a solvent and a reducing reagent.

11. The method of claim 9, wherein the solvent and a reducing reagent is ethylene glycol.

12. The method of claim 8, further involving heating of the solution of polymer and a salt precursor of a metal into the solvent.

13. The method of claim 8, further involving removal of excess of un-bound polymer onto the polymer-coated nanoparticles by washing with a first solvent, separation and redispersion of the polymer-coated nanoparticles into a second solvent to form a polymer-coated nanoparticle dispersion that is free of unbound polymer, (i.e., does not contain unbound polymer).

14. The method of claim 8, wherein the carbon nanotubes are selected from a group of single wall and multi-wall carbon nanotubes.

15. The method of claim 8, wherein the diameter of the metallic core of the polymer coated metal nanoparticles decorated carbon nanotubes is comprised in a range from 1 nm to 20 nm.

16. The method of claim 8, wherein the diameter of the metallic core of the polymer coated metal nanoparticles decorated carbon nanotubes is comprised in a range from 1 nm to 20 nm and the carbon nanotubes are single wall carbon nanotubes.

17. A method of producing metal alloy nanoparticle-decorated carbon nanotubes, the method comprising:
   forming polymer-coated metal nanoparticles by dispersing a polymer and a mixture of two or more salt precursors of metals into a solvent, reducing the mixture of metal salt precursors with a reducing reagent forming polymer coated alloy metal nanoparticles containing two or more metals;
   forming a reaction mixture by combining a first solution with a second solution, wherein the first solution comprises polymer-coated metal nanoparticles comprising metallic nanoparticles coated with a polymer, and wherein the second solution comprises carbon nanotubes; and
   heating the reaction mixture to a temperature greater than a glass transition temperature of the polymer for a time sufficient to cause the polymer-coated metal nanoparticles to bind to the carbon nanotubes forming the metal nanoparticle-decorated carbon nanotubes.

18. The method of claim 17, wherein the salt precursors of the polymer-coated metal alloy nanoparticles is selected from a group of metal ions that after reduction process form metals selected from a group of palladium, iridium, rhodium, platinum, and gold.

19. The method of claim 17, wherein an average degree of functionalization of the carbon nanotubes with carboxylic acid groups and/or hydroxyl groups is less than 3 wt % based on a total weight of the carbon nanotubes.

* * * * *